United States Patent [19]
Margelos et al.

[11] Patent Number: 5,263,494
[45] Date of Patent: Nov. 23, 1993

[54] HEAD POSITIONER FOR CEPHALOMETRIC X-RAY

[75] Inventors: George T. Margelos, Buffalo Grove; Daniel M. Filipek, Mt. Prospect, both of Ill.

[73] Assignee: Gendex Corporation, Des Plaines, Ill.

[21] Appl. No.: 787,049

[22] Filed: Nov. 4, 1991

[51] Int. Cl.$^5$ .................. A61G 15/00; A61B 19/00
[52] U.S. Cl. ..................... 128/845; 606/130
[58] Field of Search ............ 128/845; 602/16, 17, 602/18, 19; 606/130

[56] References Cited

U.S. PATENT DOCUMENTS

| | | | |
|---|---|---|---|
| 2,492,383 | 12/1949 | Jones | 128/845 |
| 3,223,087 | 12/1965 | Vladyka | 606/130 |
| 3,542,030 | 11/1970 | Hoffman | 606/130 |
| 4,256,112 | 3/1981 | Kopf | 606/130 |
| 4,341,220 | 7/1982 | Perry | 606/130 |
| 4,463,758 | 8/1984 | Patil | 606/130 |
| 4,566,444 | 1/1986 | Spolyar | 606/130 |
| 4,602,622 | 7/1986 | Bär | 606/130 |
| 4,651,732 | 3/1987 | Fredrick | 606/130 |
| 4,759,361 | 7/1988 | Gallop | 606/130 |

OTHER PUBLICATIONS

Siemens, "Fascinating Flexibility-Orthophos", pp. 1–3, 6–17, and 24.

Belmont, "X-Caliber EX 1000/ EX2000", pp. 1–3, 5 and 6, Jul. 1990.

J. Morita USA Inc., "Versaview CP Panoramic-Cephalometric X-ray", Nov. 1990.

Primary Examiner—Michael A. Brown
Attorney, Agent, or Firm—Trexler, Bushnell, Giangiorgi & Blackstone, Ltd.

[57] ABSTRACT

A head positioner for positioning a patient's head properly for a cephalometric x-ray, or other type of imaging device, and for maintaining the patient's head in a proper position throughout an imaging session, comprises a mounting portion including a mounting plate and a positioning portion connected to the mounting portion by a support member. The mounting portion includes a mounting plate and a vertical height adjustment for vertically shifting the support member and the positioning portion. The positioning portion includes a pair of sliding headpieces engagable with the patient's head for properly positioning the same for imaging. An adjusting mechanism is operatively connected to the headpieces for coaxially positioning the headpieces symmetrically in unison a variable distance apart to accept heads of different dimensions. One of the headpieces is rotatable out of alignment with the other headpiece to allow initial placement of a patient's head in the positioner.

17 Claims, 3 Drawing Sheets

HEAD POSITIONER FOR CEPHALOMETRIC X-RAY

BACKGROUND OF THE INVENTION

The present invention relates generally to a novel construction of a head positioner or alignment device useful with a cephalometric x-ray, or similar type of imaging machine, which which improves upon the head positioning devices of the prior art.

Cephalometric x-ray machines, and similar imaging devices, have become quite popular in modern medical applications. Orthodontics especially, for example, has derived significant benefits from utilization of cephalometric x-ray machines. Images or x-rays produced by these machines provide orthodontists and other professionals with a valuable diagnostic tool in their practice because these machines can produce stationary, planar images, and can produce images that are panoramic in nature. Thus, cephalometric x-ray machines present a diagnostic tool that is desired by many orthodontists.

Because of the ability of the cephalometric x-ray to provide both stationary and panoramic images of a patient, it is necessary that the head be positioned precisely prior to imaging and that this precise position be maintained throughout the entire imaging process. Accordingly, a head positioner is provided with many cephalometric x-ray units. Unfortunately, however, the head positioners of the prior art have a number of shortcomings, which leave room for improvement in several respects.

The head positioners must precisely position a patient's head, and maintain that precise positioning throughout an imaging session. To do this, some means must be provided engagable with the patient's head. Ear pieces are a common embodiment of the last-mentioned means. In the prior art, some of these ear pieces are slidably or pivotally arranged to slide or pivot laterally away from one or both sides to allow initial insertion of the patient's head therebetween, and then slide or pivot laterally inwardly to engage and position the head. These ear pieces are often spring-loaded to facilitate their pivotal movements. However, the pivoting of the ear pieces under the influence of the springs may injure the patient's head. This is undesirable. Sliding ear pieces may move outwardly only to the extent permitted by a film holder to one side, and hence, only the ear piece on the side opposite the film holder is usually moved outwardly appreciably. This also implies independent positioning of the ear pieces. With such independently positionable ear pieces, it is difficult to accurately center the patient's head.

Additionally, the ear pieces must be capable of variable separating movement with respect to each other to accommodate heads of various sizes. In order to overcome the foregoing problems, some prior art devices have employed arrangements for simultaneously symmetrically adjusting the ear pieces. These prior art positioners effected this symmetrical separating movement by a relatively complex and expensive rack and pinion-type mechanism. The cost and complexity of this mechanism often renders these positioners too expensive and too complicated for some practitioners, and also difficult and expensive to service and to repair.

Furthermore, many of the prior art positioners are wall mounted units. These wall mounted units require utilization of an adjustable patient chair in order to place the patient at an appropriate height relative to the positioner for imaging. The cost of a height-adjustable chair adds to the overall cost of employing the cephalometric x-ray unit, making it economically out of reach of some practitioners.

An additional problem with these wall mounted head positioners is that they have mounting plates which allow for mounting of the units on a wall on twelve inch centers. Because the standard wall stud placement distance is every sixteen inches along a wall, the prior art devices have to be anchored, at least in part, solely by the material of the wall itself. Due to the weight of the units, they may pull the anchors out of the wall under the influence of gravity and the forces inherent in adjusting the positioner for each patient. This causes alignment problems during imaging, to say nothing of the resultant damage to the wall.

Self-contained, pedestal mounted units which provide all of the necessary height and head positioning adjustments are also available. However, such units are extremely expensive as compared to wall mounted equipment.

The head positioner, constructed according to the teachings of the present invention, is intended to assist in solving these, as well as other problems present in head positioners of the prior art.

OBJECTS AND SUMMARY OF THE INVENTION

A general object of the present invention is to provide a new and useful head positioner for use with a cephalometric x-ray, or other type of imaging machine.

Another object of the invention is to provide a head positioner which overcomes the above-noted short comings of other, currently available head positioners.

A related object of the present invention is to provide an adjusting mechanism for headpieces used in a head positioner which is more simple and sturdy, and yet price-competitive with similar adjusting mechanisms currently available.

Another related object of the present invention is to provide a wall mounted head positioner which does not require use of an adjustable patient chair.

Yet another related object of the present invention is to provide a head positioner having a novel mounting plate allowing the positioner to be mounted entirely to studs within a wall.

A head positioner, constructed according to one aspect of the present invention for positioning a patient's head properly for a cephalometric x-ray, or other type of imaging device, and for maintaining the patient's head in a proper position throughout an imaging session, comprises a positioning portion which includes a pair of headpieces engagable with the patient's head for properly positioning the same for imaging. An adjusting mechanism is operatively connected to the headpieces for positioning the headpieces symmetrically and in unison a variable distance apart to accept heads of different dimensions.

Other aspects of the invention are set forth in the appended claims.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

DETAILED DESCRIPTION OF THE ILLUSTRATED EMBODIMENT

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

Figure 1:
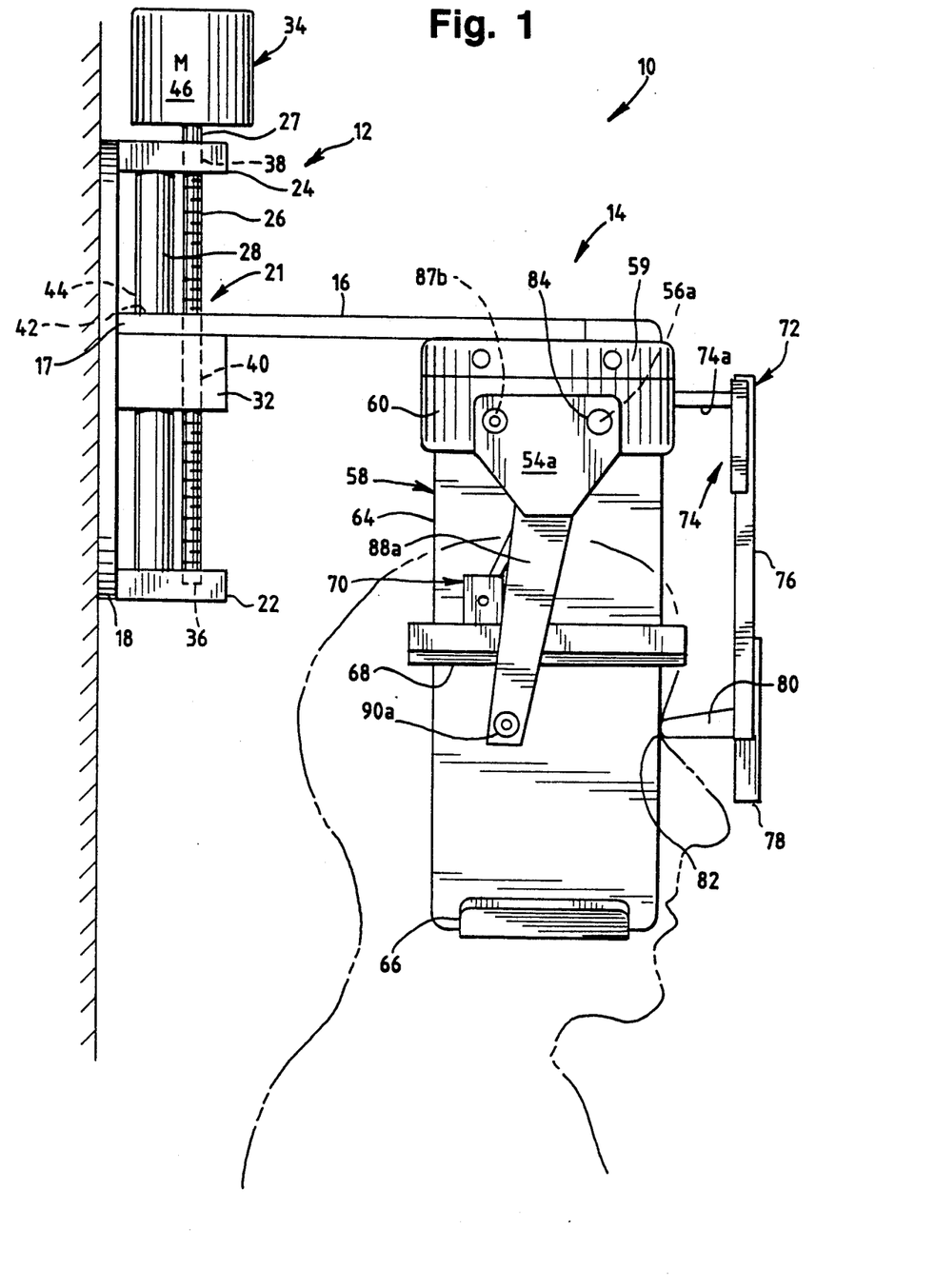
FIG. 1 is a side elevational view of a unique head positioner, constructed according to the teachings of the present invention, for use with a cephalometric x-ray machine, having a motor driven adjusting screw.
Figures 2, 6:
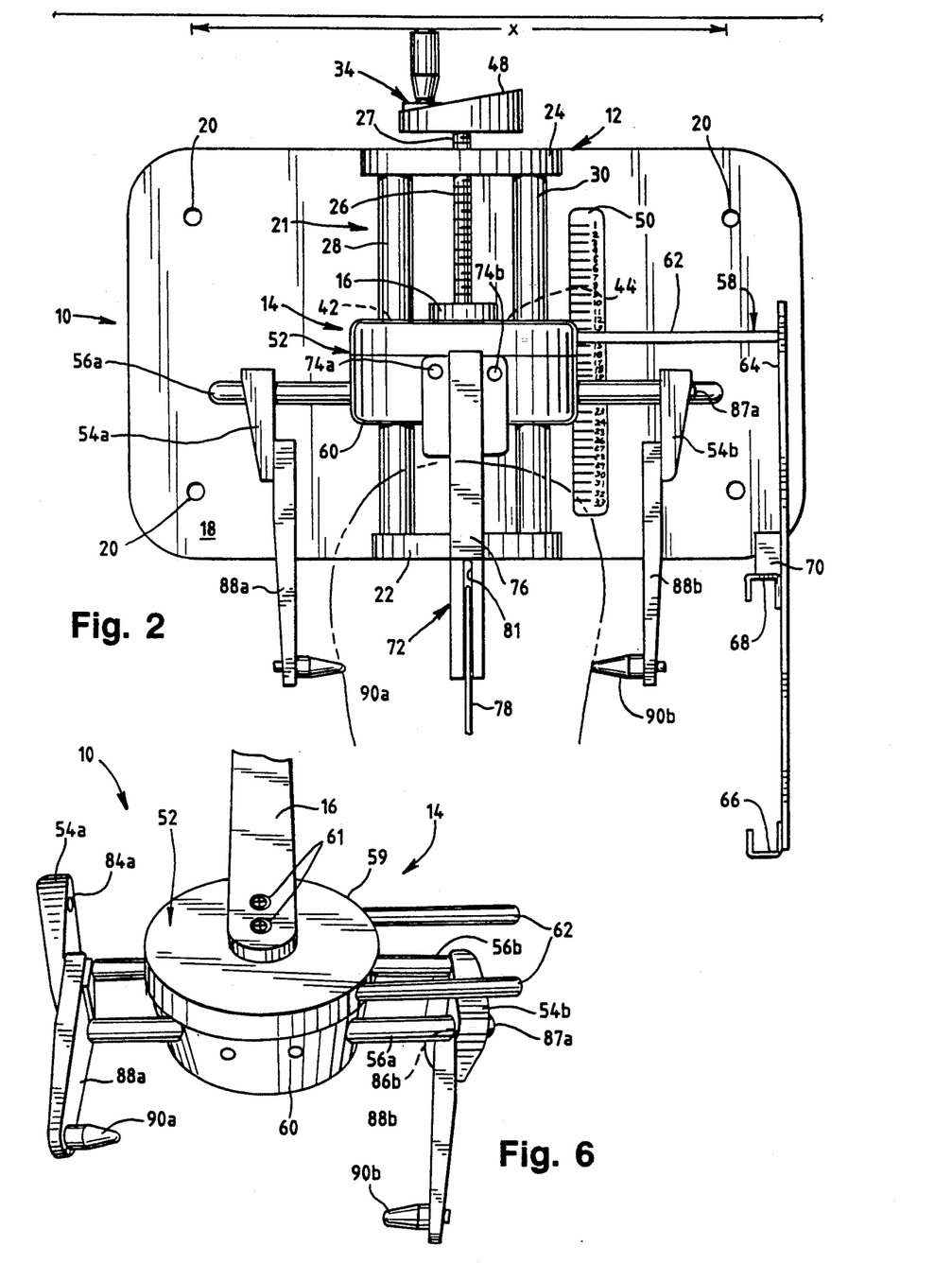
FIG. 2 is a front elevation view of a head positioner, similar to that of FIG. 1, having a manually driven adjusting screw.
FIG. 6 is a top perspective view of the head positioner of FIG. 1 with a film holder, a reference member, and a mounting portion removed for clarity.

Referring initially to FIGS. 1, 2, and 6, a head positioner 10, constructed according to the teachings of the present invention, for use with a cephalometric x-ray, or similar type of imaging device, is illustrated. The head positioner 10 is constructed so as to cooperate with an x-ray camera, not shown, of the types commonly used in medical, dental or orthodontic practice to produce x-ray images of a patient's head, or portions thereof, as shown in phantom in FIGS. 1, 2, and 6. The head positioner 10 is intended to position a patient's head in proper orientation with respect to the x-ray camera and film to produce a desired image, and to retain that position throughout the entire imaging process or session of the patient, which, at times, may amount to multiple exposures.

The head positioner 10 generally comprises a mounting portion 12 and a positioning portion 14 connected to the mounting portion 14 by an elongate support member 16. The mounting portion 12 is intended to mount the head positioner 10 to a suitable supporting surface or superstructure, such as a column, wall, or the like, as shown in FIG. 1 If a wall mounted head positioner 10 is desired, then the mounting portion 12 can be mounted directly to a wall, as will be discussed further hereinbelow. Alternatively, if a stand-alone head positioner 10 is desired, then the mounting portion 12 can be appropriately attached to a suitable column. If either of these embodiments is desired, it can be employed without the need of a height-adjustable patient chair, as will become more clear hereinafter.

As shown in FIGS. 1, 2, and 6, the mounting portion 12 generally comprises a substantially planar mounting plate 18 and height adjusting means 21 for variably vertically locating the positioning portion 14. The means 21 is connected to an end of the support member 16 opposite to an end thereof connected to the positioning portion 14. The mounting plate 18, illustrated more revealingly in FIG. 2, is preferably composed of a suitably strong, rigid material, and has a plurality of mounting apertures 20 therethrough for accepting fasteners, not shown for clarity, for mountingly attaching the plate 18 to either a wall or a column, depending upon the particular embodiment of head positioner 10 desired. The plate 18 is generally rectangular in shape, although other shapes can also be used.

Importantly, it is to be specifically noted that the mounting apertures 20 are arranged in vertically linearly oriented sets offset from each other a specific distance, labeled "X" in FIG. 2. The distance X is chosen such that the mounting plate 18 can be mounted to a surface or superstructure on sixteen inch centers. This aperture 20 disposition corresponds to the standard distance between studs comprising and supporting a wall. In this manner, fasteners mounting the plate 18 to the wall will be located on and embedded directly into the studs within that wall, thereby adding to the structural integrity of the mount. Thus, the mounting plate 18 adds further advantages to the positioner 10 over the positioners of the prior art, in which mounting holes on twelve inch centers were commonly provided, because the positioner 10 will not pull out of the supporting superstructure as easily as the prior art positioners.

As stated above, height adjusting means 21 for variably vertically locating the positioning portion 14 is affixed to the mounting plate 18, and in particular on a side thereof opposite to the side engaged by the supporting surface or superstructure. The means 21, illustrated in FIGS. 1, and 2, comprises a pair of stationary blocks 22 and 24, an adjusting screw 26, a pair of guide rods 28 and 30, and a shiftable platform 32. The height adjusting means 21 also includes drive means 34 for driving the adjusting screw 26, thereby shifting the platform 32, as will be discussed hereinafter.

The stationary blocks 22 and 24 are composed of a suitable material, such as a metal and the like, having sufficient integrity to support the other elements of the height adjusting means 21. The block 22 is fixedly mounted on the plate 18 proximate to a bottom edge thereof, and the block 24 is fixedly mounted to the plate 18 proximate to a top edge thereof so that the blocks 22 and 24 are located on the plate 18 in a substantially aligned or colinear respective orientation.

The blocks 22 and 24 each have bores 36 and 38, respectively, therein of diameters sufficient for accepting the adjusting screw 26. The blocks 22 and 24 are mounted in a substantially colinear orientation so that the bores 36 and 38 align axially when the blocks are fixedly mounted on the plate 18. In this way, the screw 26 can extend between both blocks 22 and 24. It is to be noted, however, that both bores 36 and 38 are constructed so that the screw 26 is capable of free-wheeling rotation in both bores 36 and 38 without exerting forces on the blocks 22 and 24 due to rotation of the screw 26. Also, the bore 38 extends completely through the block 24, while the bore 36 extends only approximately halfway through the block 22, as shown in FIG. 1. Thus, the screw 26 extends from approximately halfway through the block 22 upwards along the plate 18 and through the block 24. This particular orientation allows the drive means 34 to be connected to and end 27 of the screw 26 which projects from the block 24.

The guide rods 28 and 30 extend from the block 24 to the block 22 to either side of the adjusting screw 26 when the latter is disposed through the bores 36 and 38. The illustrated orientation is to have the rods 28 and 30 mounted between the blocks 22 and 24 so that the rods 28 and 30 are disposed between parallel vertical planes defined by the plate 18 and the screw 26 and aligned so as to define a further vertical plane substantially parallel to plate 18. The guide rods 28 and 30 are preferably composed of a strong material, such as a metal and the like, and are substantially cylindrical in form, although other shapes are permissible. The rods 28 and 30 serve to maintain the relative positioning of the blocks 22 and 24, and also serve to restrict and to guide the shifting motion of the platform 32. The rods 28 and 30 are, accordingly, substantially smooth and free of burrs to facilitate shifting of the platform 32 thereon.

The platform 32 is substantially planar having three bores therethrough, specifically, an internally threaded screw bore 40, a substantially smooth left rod bore 42, and a substantially smooth right rod bore 44. All of the bores 40, 42, and 44 extend through the entire thickness of the platform 32. The rod bores 42 and 44 are of dimensions sufficient to accept the rods 28 and 30, respectively.

The threads on the screw bore 40 are configured to engage and cooperate with threads on the adjusting screw 26 so that rotation of the adjusting screw 26 caused by the drive means 34 positively shifts the platform 32 along the screw 26 and the rods 28 and 30 between the blocks 22 and 24. The effective distance between the blocks 22 and 24 is sufficient to allow the platform 32 to move the positioning portion 14 through a range of positions sufficient to properly position the positioner 10 about a patient's head, without requiring a height-adjustable patient chair or the like.

The drive means 34 is shown disposed on a side of the block 24 opposite to the side thereof facing the block 22, and can take on a number of different forms. If it is desired to operate the positioning portion 14 and drive the screw 26 automatically, the drive means 34 can be a drive motor 46, shown diagrammatically in FIG. 1, operatively connected to the screw 26 is appropriate fashion. Alternatively, if it is desired to drive the screw 26 manually, the means 34 can be in the form of a hand crank 48, as illustrated in FIG. 2. With either embodiment, the same degree of positive shifting of the platform 32 is achievable.

As noted above, the shiftable platform 32 is constructed to provide sufficient support to the positioning portion 14. Accordingly, the illustrated platform 32 is of dimensions sufficient to extend from the screw 26 rearwardly to slidably engage the plate 18. In this manner, the sliding engagement between the plate 18 and the platform 32 assists in providing the necessary support to the positioning portion 14.

The mounting portion 12 is connected to the positioning portion 14 by means of the support member 16, as indicated above. One end of the support member 16 is fixedly mounted on the platform 32 so that shifting movement of the platform 32 causes corresponding shifting movement of the positioning portion 14. In this way, the positioner 10 can be utilized without the need of a height-adjustable patient's chair.

In the illustrated construction, the elongate support member 16 is substantially rectangular in construction having a length sufficient to lend necessary support to the positioning portion 14, and to provide appropriate space to accommodate proper positioning of the patient, the camera, and other equipment and personnel needed to perform the imaging of the patient. To facilitate respective proper alignment of the camera (not shown) and the positioner 10 for imaging, a metered scale 50 is provided on the mounting plate 18 in an appropriately operative location, as shown in FIG. 1. The camera is usually placed at a 60 inch center to center spacing with the head positioner 10 and on the same wall surface. In most installations, both the camera and the head positioner are mounted at a fixed height, properly aligned. In the present invention, it is envisioned that the camera will also be height-adjustable, and will have a similar scale. Thus, proper alignment of the camera with the positioner 10 can be achieved by aligning the scale 50 with the scale on the camera, provided the two scales have been properly aligned during installation.

The end 17 of the member 16 connected to the platform 32 may extend across, and be mounted to, the entire width and depth of a top surface portion of the platform 32. This produces much the same engagement of end 17 with the plate 18 as disclosed above with respect to the platform 18, thereby lending support to the positioning portion 14. Additionally, bores, not shown for clarity, but constructed substantially similarly to the bores 40, 42 and 44 may be provided within the member 16 for accepting the screw 26 and the guide rods 28 and 30, thereby increasing the support provided to the positioning portion 14.

An end of the support member 16 opposite to the end thereof mounted on the platform 32 is connected to the positioning portion 14. The positioning portion 14 can serve at least two functions: to position the patient's head, and to hold the film in proper relation to the head for imaging. Appropriate means are provided to perform each function.

As illustrated in FIGS. 1, 2, and 6, the positioning portion 14 comprises an adjusting mechanism 52, a pair of headpieces 54a and 54b variably shiftably connected to the adjusting mechanism 52 by a pair of guide bars 56a and 56b, and a film holding device 58. The adjusting mechanism 52 is contained within a housing 60 which protectively holds the operative elements of the mechanism 52. The housing 60 is rotatably mounted to a housing cover member 59 which is affixed to the support member 16 by fasteners 61, shown in FIG. 6. Thus, the housing 60, the adjusting mechanism 52, guide bars 56a and 56b, and headpieces 54a and 54b are capable of rotation. This provides added convenience to the operator and patient.

The film holding device 58 comprises a pair of supporting arms 62 extending from the housing cover 59 an appropriate distance to accommodate the patient's head, and to properly position the film for imaging exposure. The support arms 62 may be slidably adjustably connected to the housing cover 59. A substantially planar film support member 64 depends substantially perpendicularly from an end of the arms 62 opposite to the ends thereof connected to the housing cover 59, extending a certain distance sufficient to properly support and position the film. An end of the film support member 64 opposite the arm 62 terminates in a fixed bracket 66 which cooperates with a parallel adjustable bracket 68 for holding the film. The bracket is also mounted to the support member 64 and is adjustable by appropriate means 70 to a selectable position parallel to and spaced a selectable distance from bracket 62 so as to accommodate films of various sizes, and to hold film in various orientations for imaging.

A reference member 72 extends from the housing 60 at a point rotated substantially ninety degrees from the location of the headpieces 54a and 54b on the housing 60. The reference member 72 comprises a projecting portion 74 comprising a pair of rods 74a and 74b, slidably extending from the housing 60, and a depending portion 76 which extends downwardly substantially perpendicularly from an end of the projecting portion 74 opposite to the end thereof connected to the housing 60. The reference member 72 can serve at least two functions, namely, providing a contact point for positioning engagable with the patient, and providing a reference which will show up on a developed film exposure.

To perform these functions, the reference member 72 includes a scale 78 and a nose piece 80 connected to the depending portion 76. The depending portion 76 has a slot 81 therein extending longitudinally inwardly from a free outer end thereof of dimensions sufficient to accept and retain the scale 78. The scale 78 is substantially rectangular in shape and depends from the depending portion 76 substantially linearly therewith, and is composed of a material, such as a metal, which will image clearly on a developed film exposure. Thus, a person interpreting the exposure will have a definite reference point or points useful in making his interpretations of the image.

The nose piece 80 extends from the depending portion 76 substantially perpendicularly inwardly towards the housing 60. The nose piece 80 has a curved tip 82 which is intended to slide along and engage the bridge of a patient's nose as the positioning portion 14 is adjusted vertically, as shown in FIG. 1. Thus, the nose piece 80 provides a point of contact between the patient and the positioner 10, thereby facilitating proper positioning of the patient with respect to the positioner 10, film, and camera, and also facilitating maintenance of that positioning throughout the imaging session. It is to be noted that the projecting portion 74 can be variably extended relative to the housing 60, thereby allowing corresponding movement of the depending portion 76 to accommodate patients of differing dimensions.

Figures 3, 4, 5:
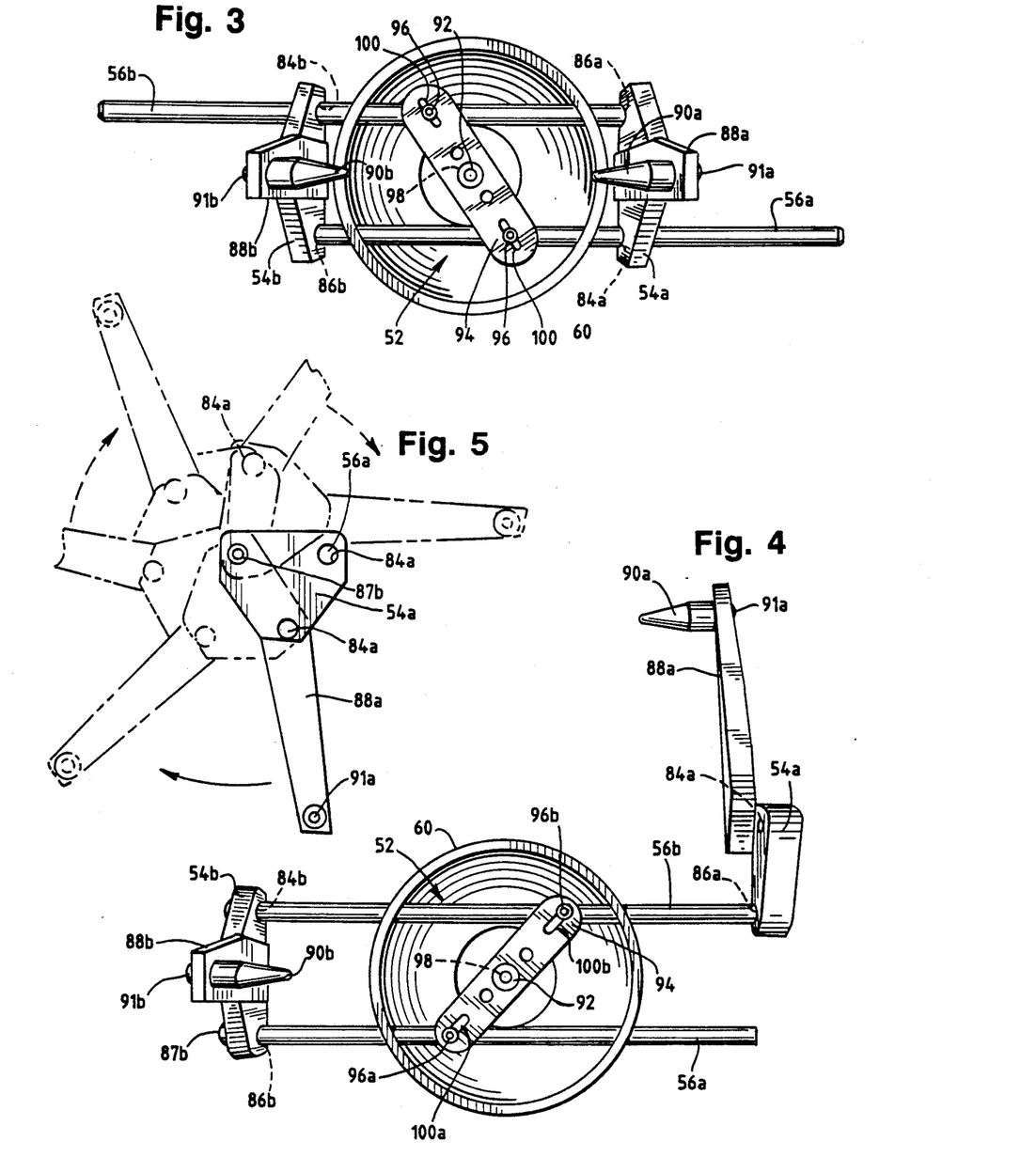
FIG. 3 is a bottom view of an adjusting mechanism utilized in the head positioners of the invention with a bottom cover removed, showing the mechanism shifting headpieces into a collapsed position.
FIG. 4 is a view, similar to that of FIG. 3, showing the mechanism shifting the headpieces into an extended position, with one headpiece removed from and rotated with respect to guide bars.
FIG. 5 is a sequential view of a headpiece rotating about a guide bar of the positioner.

Referring also to FIGS. 3 through 5, the guide bars 56a and 56b extend through the housing 60 on both sides thereof in an essentially parallel fashion. In a preferred construction, the guide bars 56a and 56b are substantially cylindrical, although other shapes are possible. Importantly, the surfaces of the bars 56a and 56b are substantially smooth and free of burrs. This allows the headpieces 54a and 54b to freely slide therealong between a fully extended position and a fully retracted position, as will be more fully described hereinbelow. Also, it is to be noted that one of the bars 56a or 56b is slightly longer than the other. This allows for disengagement of one of the headpieces 54a or 54b from one of the bars 56a or 56b, and for pivotal rotation of that headpiece 54a or 54b about that bar 56a or 56b, as will be more fully discussed later.

The headpieces 54a and 54b are substantially identical in construction. Specifically, the headpieces 54a and 54b each have a smooth through bore 84a and 84b and another bore 86a and 86b having a closed end. Both bores 84a and 84b are of dimensions to accept the bars 56a and 56b, in a close, sliding fit. Because the bores 84a and 84b extend through the headpieces 54a and 54b, the headpieces 54a and 54b can slide along the bars 56a and 56b, which extend through the bores 84a and 84b.

However, because the bores 86a and 86b have closed ends, the bars 56a and 56b cannot slide freely through the bores 86a and 86b. More specifically, one of the bars 56a or 56b is inserted into the bore 86a and 86b in each headpiece 54a and 54b, and is fixedly mounted therein, for example, by suitable fasteners 87a and 87b. Accordingly, as the headpieces 54a and 54b slide along the effective lengths of one of the bars 56a and 56b through the bores 84a and 84b, the headpieces 54a and 54b remain fixed to the other bar 56b and 56a at the bores 86a and 86b.

Thus, in order for the headpieces 54a and 54b to be coaxially positioned a variable distance apart to accept heads of different sizes, the headpieces 54a and 54b are oriented on the bars 56a and 56b such that, for example, the bar 56b is fastened at one end to the bore 86a of the headpiece 54a, and the bar 56b slidably extends through the housing 60 and through the bore 84b in the headpiece 54b. The bar 56a is fastened at one end to the bore 86 of the headpiece 54b, and the bar 56a slidably extends through the housing 60 and through the bore 84a in the headpiece 54a.

Also, because the bores 84a and 84b extend completely through the headpieces 54a and 54b, and because the bar 56a is shorter in length than the bar 56b, the headpiece 54a can become disengaged from the shorter bar 56a at the bore 84a, while headpiece 54b still remains upon the longer bar 56b at the bore 84b. This allows the headpiece 54a and the bar 56b to rotate freely around the axis of the bar 56b, as shown in FIGS. 4 through 6, to facilitate insertion of a patient's head into and removal of a patient's head from the positioner 10, and to facilitate proper orientation of the positioner 10 with respect to the patient. The full range of rotation of the headpiece 54a or 54b is limited to a substantially two hundred and seventy degree arc due to encountering the bar 56a at this amount of rotation, as best viewed in FIG. 5.

Arms 88a and 88b depend downwardly from each headpiece 54a and 54b a distance sufficient to allow placement of terminal ends thereof adjacent a patient's ears when the patient's head is located in the positioner 10, as shown in FIGS. 1, 2, and 6.

Ear pieces 90a and 90b extend substantially perpendicularly away from the arms 88a and 88b inwardly towards each other at the terminal ends of the arms 88a and 88b. The ear pieces 90a and 90b are substantially conical in shape, and are intended to gently contact and engage a patient's ears when properly positioned for imaging. Thus, the ear pieces 90a and 90b provide additional points of contact between the positioner 10 and a patient, thereby assuring attainment of proper positioning for imaging, and maintenance of that positioning throughout the imaging session. The ear pieces 90 may be composed of a material that will shown up in a developed film image, however, in the illustrated embodiment, the ear pieces 90a and 90b are attached to the arms 88a and 88b by fasteners 91a and 91b composed of such a material. By either method, the ear pieces 90a and 90b may provide additional reference points useful in interpreting the developed film image of the patient.

As stated above, the headpieces 54a and 54b are disposed in a sliding arrangement so that they can be coaxially positioned a variable distance apart for accepting differently sized heads of patients. This variable distance positioning is performed by the adjusting mechanism 52, the operative elements of which are illustrated in FIGS. 3 and 4.

FIGS. 3 and 4 are bottom views of the adjusting mechanism 52 with a bottom portion of the housing 60 removed, revealing the operative elements. The operative elements of the mechanism 52 include a central stationary shaft 92, a crank arm 94, and a fastener or boss 96a and 96b attached to each bar 56a and 56b. The bars 56a and 56b are shown projecting through either side of the housing 60, which is provided with pairs of aligned through apertures for this purpose.

The crank arm 94 is essentially a longitudinally elongate member having a centrally located bore of dimensions sufficient to accept the shaft 92 such that the crank arm 94 rotates freely on the shaft 92. The crank arm 94 has two longitudinally extending symmetrically formed and located slots 100a and 100b therein adjacent opposite ends of the arm 94. The slots 100a and 100b define a line substantially perpendicular to an axis of rotation of the arm 94. The slots 100a and 100b are of dimensions sufficient to accept the bosses 96a and 96b so that the bosses can slide along the length of the slots.

The bosses 96a and 96b extend through the slots 100a and 100b and each is fixedly and symmetrically mounted on one of the bars 56a and 56b. The length of the slots 100a and 100b is chosen such that the bosses 96a and 96b travel from one end of the slots 100a and 100b to the other as the headpieces 54a and 54b are shifted between a retracted position, illustrated in FIG. 3, and an extended position, illustrated in FIG. 4. As the bosses 96a and 96b shift within the slots 100a and 100b, the crank arm 94 is caused to rotate about the shaft 92. The foregoing arrangement is such that the bars 56a and 56b move symmetrically and in unison between the two positions because their movement is operatively coupled by the cooperation of the bosses 96a and 96b with the slots 100a and 100b, accompanied by the attendant rotation of the arm 94 on the shaft 92. Thus, the headpieces 54a and 54b are symmetrically positioned in unison at a variable distance to accept a patient's head.

An example of the relative lengths of the bars 56a and 56b discussed hereinabove is illustrated in FIG. 4. Therein, the bar 56a is shown as being slightly shorter in effective length than the bar 56b. Because the bar 56a is shorter, the bore 84a in the headpiece 54a can become disengaged from the bar 56a when the headpieces 54a and 54b are in the extended position. The headpiece 54a is still firmly attached to the bar 56b at the bore 86a. Thus, disengagement of the headpiece 54a does not inhibit uniform coaxial shifting of the headpieces 54a and 54b.

Moreover, disengagement of the headpiece 54a from the bar 56b facilitates rotation of that headpiece 54a about the bar 54a, as described above as illustrated in FIG. 5. The range of rotation is limited by contact of the arm 88a associated with the headpiece 54a with the bar 56b upon rotation through a substantially two hundred and seventy degree arc. The rotatability of the headpiece 54a facilitates entry of the patient into the positioner 10, and also eliminates the need to have the head or ear pieces spring-loaded to engage the patient's head, thereby reducing the probability of injury to the patient. It is to be noted that, although the positioner 10 has been disclosed specifically with the headpiece 54a being disengagable and rotatable, the relative lengths of bars 56a and 56b could be reversed so that headpiece 54b can be disengagable and rotatable (if film holder 58 is removed) instead without departing from the scope of the invention. If desired, bars 56a and 56b could be equal in length so that both headpieces 54a and 54b can be disengagable and rotatable.

With the construction of the positioner 10 thusly disclosed, the function and utilization thereof will now be discussed. First, an operator must decide if he desires a wall mounted or a stand-alone, column mounted positioner 10. For the former, the operator should locate a vertical stud within the wall. This being done, the plate 18 of the positioner 10 can be mounted to the wall at the stud. Because the plate 18 has mounting apertures 20 located on sixteen inch centers, once one stud is located and one vertical set of apertures 20 is aligned therewith, the other vertical set(s) will automatically align with other studs in the wall. This is due to the fact that the standard placement for studs is every sixteen inches. For the latter, column mounted arrangement, the plate 18 can be attached to a column by appropriate means in a similar fashion. Now, the positioner 10 is ready for employment.

The patient assumes an appropriate position with respect to the positioner 10 so that the patient's head can be inserted therein for imaging. This appropriate position could be sitting, if the imaging unit includes a patient chair, or standing. To facilitate insertion of the patient's head into the positioner 10, one of the headpieces 54a or 54b should be disengaged from and rotated with respect to one of the bars 56a or 56b. For purposes of clarity, the same assumptions will be made as were made in the above-discussed example.

The headpieces 54a and 54b are shifted into the extended position by the application of an appropriately directed force to either or both of the headpieces 54a or 54b. It does not matter to which headpiece 54a or 54b the force is applied because the motion of the headpieces 54a and 54b is coupled by the cooperation of the bosses 96 on the bars 56a and 56b and the slots 100 in the crank arm 94.

Under the influence of the applied force, the headpieces 54a and 54b move coaxially along the bars 56a and 56b in opposite directions away from the adjusting mechanism 52 until the bosses 96a and 96b approach corresponding terminal ends of the slots 100a and 100b. When the bosses 96a and 96b approach the terminal ends, the headpieces 54a and 54b have reached the extended position, as shown in FIG. 4. Interference between the bosses 96a and 96b and the ends of the slots 100a and 100b positively limits the distance the headpieces 54a and 54b can extend away from each other, thereby assuring that the bars 56a and 56b will not become operatively dislodged from the housing 60 or from the adjusting mechanism 52.

Once the headpieces 54a and 54b are in the extended position, the headpiece 54a can be disengaged from the bar 56a at the bore 84a in the headpiece 54a. The headpiece 54a can now be freely rotated up and out of the way, thereby allowing easy and free insertion of the patient's head into the positioner 10. Coming to rest upon the bar 56b is sufficient to maintain the headpiece 54a in its fully rotated, out of the way disposition.

The patient's head is inserted into the positioner 10 as illustrated in FIGS. 1 and 2. If the positioner 10 is too high or too low with respect to the patient, the drive means 34 can be actuated, thereby driving the screw 26 to vertically shift the shiftable platform 32 along the guide rods 28 and 30 between the blocks 22 and 24. The means 34 is actuated until the positioner 10 is in the proper position with respect to the patient's head. The determination of this proper position can be assisted by utilization of the nose piece 80 and/or one or both ear pieces 90a and 90b. The variable vertical positioning of the positioner 10 by utilization of the means 34 allows the positioner 10 to be utilized without the need of an adjustable patient's chair.

Either before or after the means 34 has properly positioned the positioner 10 vertically with respect to the patient, the headpiece 54a can be rotated back into its original position where it is rejoined with the bar 56a. To rejoin the headpiece 54a with the bar 56a, the bore 84 is aligned with the bar 56a, and an appropriately directed force is applied to at least one of the headpieces 54a or 54b. For the reasons stated above, it does not matter to which headpiece 54a or 54b the force is applied. The force causes the bar 56a to be inserted into the bore 84 thereby re-engaging the headpiece 54a with the bar 56b.

At this point, the position of the nose piece 80 is adjusted, possibly along with the aid of vertical positioning of the positioner 10 by the drive means 34, so that the curved tip 82 confronts and contacts the bridge of the patient's nose, thereby providing a point of contact between the positioner 10 and the patient's head. Now, the headpieces 54a and 54b can be moved in unison towards the collapsed position until the ear pieces 90a and 90b contact the patient's ears.

To do this, an appropriately directed force is applied to at least one of the headpieces 54a or 54b. This force causes the headpieces 54a and 54b to slide coaxially along the bars 56a and 56b a variable distance depending upon the dimensions of the patient's head. The adjusting mechanism 52 assures that the coaxial sliding of the headpieces 54a and 54b on the bars 56a and 56b is symmetrical with respect to the housing 60. In his way, the patient's head is properly positioned for imaging.

The film can now be added to the film holding device 58 and placed in the brackets 66 and 68 in a desired orientation. With the patient's head in the proper position, the camera can be placed proximate to the patient's head for exposing the film and imaging the patient. To insure proper alignment of the camera (not shown) with the positioner 10, and therefore with the patient's head, the camera is mounted such that the scale 50, shown in FIG. 2, on the mounting plate 18 is appropriately aligned with a corresponding scale on the camera. After the imaging session is complete, the patient can be removed from the positioner 10 by reversing the above-discussed process.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention claimed is as follows:

1. A head positioner for positioning a patient's head properly for a cephalometric x-ray, or similar type of imaging device, and for maintaining the patient's head in a proper position throughout an imaging session, the head positioner comprising: a positioning portion for positioning a patient's head; the positioning portion including ak housing and a pair of headpieces slidably mounted to the housing and engageable with the patient's head for properly positioning the same for imaging, and an adjusting mechanism operatively connected to the headpieces for positioning the headpieces symmetrically and in unison a variable distance apart to accept heads of different dimensions; and further including a pair of parallel, spaced apart guide bars slidably extending through said housing for connecting the headpieces to the adjusting mechanism; each headpiece being fixedly connected to one of the guide bars at one side of the housing, and being slidably connected to the other of the guide bars at said one side of the housing; each headpiece being fixedly connected to the guide bar to which the other headpiece is slidably connected; and wherein the relative lengths of the guide bars are selected such that at least one of the headpieces is disengageable from the guide bar to which it is slidably connected and rotatable about an axis defined by the guide bar to which it is fixedly connected to facilitate initial placement of the patient's head in the head positioner; and further including a mounting portion including a mounting plate for mounting the head positioner to a surface; a support member extending from the mounting portion for supporting the positioning portion; and vertical height adjustment means for selectably adjusting the vertical height of the support member and the positioning portion relative to the surface; wherein the vertical height adjustment means comprises a platform having an internally threaded bore therethrough sufficient to accept a drive screw; a drive screw vertically threadably extending through the bore and rotatably coupled to the mounting plate; and threads on the screw cooperating with threads in the bore when the screw is rotated such that the platform positively shifts the support member and the positioning portion vertically relative to the mounting plate.

2. A head positioner as defined in claim 1 wherein the mounting plate is mountable on a wall, and further including a plurality of mounting apertures disposed through the mounting plate for accepting fasteners for mounting the plate to the wall; the mounting apertures being arranged on sixteen inch centers.

3. A head positioner as defined in claim 1 wherein the support member is connected between the platform and the positioning portion.

4. A head positioner as defined in claim 1 further comprising a top stationary block and a bottom stationary block attached to the mounting plate; the blocks having bores therein sufficient to accept the screw freely rotatably therein; at least one guide rod extending between the blocks; the platform having at least one bore therethrough for slidably accepting the guide rod so that the platform can slide along the guide rod under the influence of the rotation of the screw and cooperation of the threads of the bore and the screw; and the blocks positively limiting the range through which the platform can shift vertically.

5. A head positioner as defined in claim 4 wherein two guide rods extend between the blocks flanking the screw on opposite sides thereof, and two complementary bores in the platform respectively slidably receive the guide rods.

6. A head positioner as defined in claim 1 further comprising means for driving the screw operatively connected to the screw for shifting the platform.

7. A head positioner as defined in claim 6 wherein the means for driving the screw comprises one of a drive motor and a hand crank.

8. A head positioner as defined in claim 1 further comprising a scale disposed on the mounting portion for aligning the head positioner with an imaging device.

9. A head positioner as defined in claim 1 wherein the disengagable headpiece is capable of rotation through a substantially two hundred and seventy degree arc.

10. A head positioner as defined in claim 1 wherein each of the headpieces has two bores for accepting the guide bars; at least one of the two bores extending through the headpiece.

11. A head positioner as defined in claim 1 further comprising a reference member connected to the positioning portion; the reference member including a scale composed of a material visible on a developed film image and a nose piece coupled with the reference member and engagable with a bridge of a patient's nose for verifying the positioning of the patient's head.

12. A head positioner as defined in claim 1 wherein the adjusting mechanism comprises a housing having opposed pairs of through openings, a stationary shaft mounted in the housing, a crank arm rotatably mounted on the shaft and within the housing, elongate slots disposed on opposite ends of the crank arm projecting means disposed on the guide bars extending through the slots and slidable along the slots; the guide bars being capable of sliding movement through the through openings of the housing; and sliding movement of either guide bar causing rotation of the crank arm by cooperation of the projecting means and the slots, which are configured and located for causing symmetrical sliding movement of the guide bars and symmetrical positioning of the headpieces.

13. A head positioner as defined in claim 1 further comprising a film holding device connected to the positioning portion for holding film for imaging.

14. A head positioner as defined in claim 13 wherein the film holding device comprises a support arm extending from the adjusting mechanism; a film support member depending from the support arm; and brackets disposed on the film support member for releasably holding film.

15. A head positioner as defined in claim 14 wherein the position of one of the brackets is adjustable relative to the other bracket for accommodating films of various sizes and in various orientations.

16. A head positioner as defined in claim 1 wherein each headpiece includes a depending arm; and the arm bearing an ear piece engagable with a patient's ear for facilitating positioning of the patient's head.

17. A head positioner as defined in claim 1 wherein at least one of the headpieces is capable of rotation through a substantially two hundred and seventy degree arc.

* * * * *